United States Patent [19]

Tanii et al.

[11] Patent Number: 5,400,769
[45] Date of Patent: Mar. 28, 1995

[54] ELECTRICALLY BENDABLE ENDOSCOPE APPARATUS HAVING CONTROLLED FIXED BENDING SPEED

[75] Inventors: Yoshiyuki Tanii; Hiroki Hibino, both of Hachioji, Japan

[73] Assignee: Olympus Optical Co., Ltd., Tokyo, Japan

[21] Appl. No.: 989,945

[22] Filed: Dec. 10, 1992

Related U.S. Application Data

[63] Continuation-in-part of Ser. No. 835,571, Feb. 14, 1992, abandoned.

[30] Foreign Application Priority Data

Feb. 18, 1991 [JP] Japan ................ 3-023468
Nov. 21, 1991 [JP] Japan ................ 3-306410

[51] Int. Cl.$^6$ .............................................. A61B 1/04
[52] U.S. Cl. ............................................. 128/4; 128/6
[58] Field of Search ..................... 128/4, 6, 7-10, 128/656-658, 772; 604/95, 280

[56] References Cited

U.S. PATENT DOCUMENTS 4,559,928 12/1985 Takayama .................... 128/6
4,930,494 6/1990 Takehana et al. ............ 128/4
4,941,454 7/1990 Wood et al. .................. 128/4
4,982,725 1/1991 Hibino et al. .
5,060,632 10/1991 Hibino et al. ................ 128/6

FOREIGN PATENT DOCUMENTS 58-69523 4/1983 Japan .
63-59329 11/1988 Japan .
1-317423 12/1989 Japan .
2-12571 3/1990 Japan .

Primary Examiner—Richard J. Apley
Assistant Examiner—John P. Leubecker
Attorney, Agent, or Firm—Armstrong, Westerman, Hattori, McLeland & Naughton

[57] ABSTRACT

In response to the operation of a bending operation switch, a controlling circuit switches on/off a plurality of transistors of a driving circuit, controls the polarity of a voltage applied to a motor or does not apply the voltage and, on the other hand, controls the voltage applied to the motor to be on/off while monitoring the rotating speed of the motor through an encoder to thereby drive and control the motor at a predetermined speed which can be variably set steppedly so that an endoscope bendable part may be bent at a fixed speed.

1 Claim, 15 Drawing Sheets

ELECTRICALLY BENDABLE ENDOSCOPE APPARATUS HAVING CONTROLLED FIXED BENDING SPEED

This application is a continuation-in-part of application Ser. No. 07/835,571, filed Feb. 14, 1992, now abandoned.

BACKGROUND OF THE INVENTION

1. Field of the Invention

This invention relates to an electrically bendable endoscope apparatus which is bendable at a fixed speed.

2. Description of the Related Art

Recently, there has been extensively used an endoscope whereby organs within a body cavity can be observed by inserting an elongate insertable part into the body cavity or, as required, various therapeutic treatments can be made by using a treating instrument inserted into a treating instrument channel.

Also, an industrial endoscope has been extensively utilized to observe and inspect flaws and corrosions within pipings, such as in a boiler, gas turbine engine and chemical plant and within the body of an automobile engine.

Such an endoscope generally has a mechanism for bending a bendable part on the tip part side and is provided with such electrically driving means as an electric motor to drive this bending mechanism. Such an electrically bendable endoscope is combined with a bending controlling apparatus for controlling the bending of this endoscope and a light source apparatus so as to form an electrically bendable endoscope apparatus.

As shown in the publications of Japanese Patent Application Laid Open No. 317423/1989, Japanese Patent Application Publication Nos. 12571/1990 and 59329/1988 and Japanese Patent Application Laid Open No. 69523/1983, the disclosed electrically bendable endoscope apparatus has, in the bending controlling apparatus, a controlling means for controlling the bending speed with the bending operation switch which controls time, operated amount and operated force amount in order to improve its operability.

However, in the conventional electrically bendable endoscope apparatus, as the bending speed varies with the bending operation switch controlling time, operated amount, Operated force amount or operated state, it will take time to be accustomed to the operation and particularly beginners will find it hard to operate the bending operation switch. Therefore, in the above-mentioned apparatus, with a slight operation, the bending will be large, will be quick or will quickly become slow, what degree of operation may be made to obtain a predetermined bent angle will not be able to be easily caught and, in order to make an operation as desired, one must be skilled in the operation.

Also, as shown in the publication of Japanese Patent Application Laid Open No. 69523/1983, a fine adjusting bending switch is provided besides the bending operation switch but the bending speed is not controlled thereby to be fixed (constant). Therefore, there is the problem that, when the bending angle is large, the torque of the motor will be weaker than the tension of the wire for bending, therefore the bending speed will be low and the fine adjusting operation will not be able to be well made.

U.S. Pat. No. 4,982,725 discloses an endoscope apparatus whereby, in case the insertable part bends to contact the object to be inspected, it will be quickly detected and further the contact will be avoided to improve the safety of the endoscope inspection.

SUMMARY OF THE INVENTION

An object of this invention is to provide an electrically bendable endoscope apparatus which can be easily operated by a beginner to fix and stabilize the bending speed.

Another object of this invention is to provide an electrically bendable endoscope apparatus which can be easily operated by a beginner to fix and stabilize the bending speed even with an increase of the load applied to the bendable part.

Another object of this invention is to provide an electrically bendable endoscope apparatus wherein, in case the load applied to the bendable part is too large, the bending operation will be stopped to increase safety.

Another object of this invention is to provide an electrically bendable endoscope apparatus wherein, even in case the bendable part is vibrated, the vibrating speed of the bendable part will be fixed and stabilized to improve the endoscope insertability.

Another object of this invention is to provide an electrically bendable endoscope apparatus wherein the bendable part is prevented from unexpectedly moving to hurt the interior of a body cavity at the time of starting the apparatus thus increasing safety.

Briefly, this invention comprises a bending mechanism for bending a bendable part provided in an endoscope insertable part, a driving means for driving the above-mentioned bending mechanism, an operating means for giving an instruction to cause a bending operation in the above-mentioned bendable part, and a controlling means for controlling the above-mentioned driving means to drive the above-mentioned bending mechanism at a fixed speed. The endoscope bendable part is therefore bent at a fixed speed.

The other features and advantages of the present invention will become apparent enough with the following detailed description.

BRIEF DESCRIPTION OF THE DRAWINGS

FIG. 1 is a schematic formation diagram of a bending mechanism, bending driving system and controlling system.

FIG. 2 is a general formation diagram of an electrically bendable endoscope apparatus.

FIG. 3 is an electric circuit diagram showing an example of a driving circuit.

FIG. 4 is a controlling operation flow chart of a bending operation and bending speed.

FIG. 5 is a setting operation flow chart of a speed setting flag.

FIG. 6 is a switching operation flow chart of a bending speed.

FIG. 7 is a schematic formation diagram of a bending mechanism, bending driving system and controlling system.

FIG. 8 is an electric circuit diagram showing an example of a driving circuit.

FIG. 9 is a flow chart showing a bending operation and driving setting operation.

FIG. 10 is a set speed flag setting operation flow chart.

FIG. 11 is a constant speed controlling voltage switching operation flow chart.

FIG. 12 is a block diagram showing the formation of a bending motor controlling apparatus.

FIG. 13 is a circuit diagram showing the formation of a motor driving circuit.

FIG. 17 is a formation diagram showing bending pieces of a bendable part in the fifth embodiment of the present invention.

FIG. 18 is a block diagram showing the formation of bending angle detection in the fifth embodiment of the present invention.

DESCRIPTION OF THE PREFERRED EMBODIMENT

The first embodiment of the present invention shall be explained with reference to the drawings.

Figure 2:
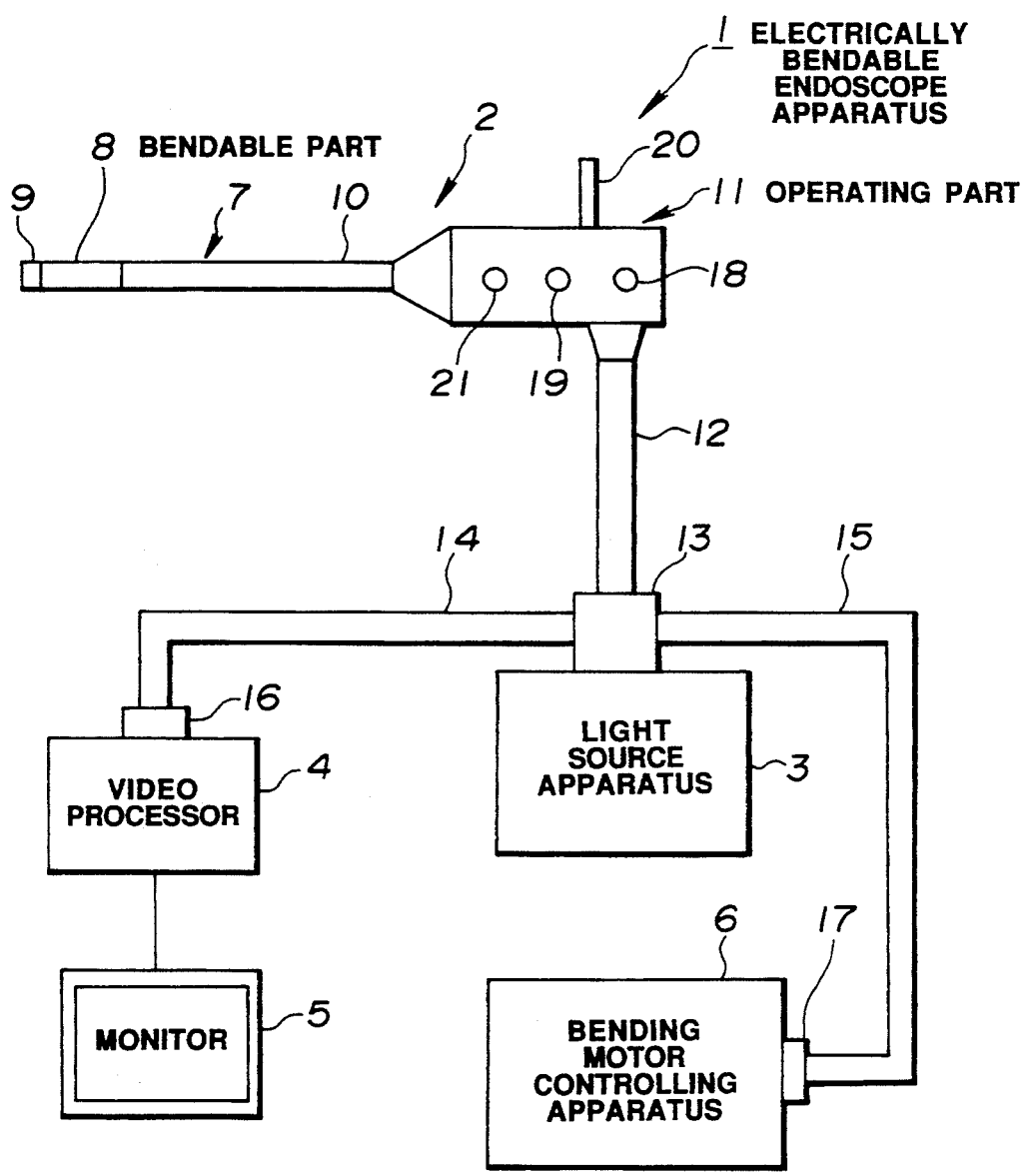

The electrically bendable endoscope apparatus 1 shown in FIG. 2 comprises an electronic type electrically bendable endoscope 2 having a bendable part 8 provided on the tip side of a fine long insertable part 7, a light source apparatus 3 for feeding the electrically bendable endoscope 2 with an illuminating light, a video processor 4 for processing an image signal output by the electrically bendable endoscope 2 to be a reference video signal, a monitor 5 for inputting the video signal output by the video processor 4 and for displaying an endoscope observed image and a bending motor controlling apparatus 6 for controlling the bending operation of the bendable part 8 of the electrically bendable endoscope 2.

The above-mentioned insertable part 7 has a tip part 9, the above-mentioned bendable part 8 and a flexible tube part 10 having a flexibility in the order from the tip side. Also, the electrically bendable endoscope 2 is provided with an operating part 11 provided as connected to the rear end of the flexible tube part 10. A flexible universal cable 12 is extended sidewise from this operating part 11 and is provided at the end with a connector 13 removably connected to the above-mentioned light source 3. A signal cable 14 and driving cable 15 are extended from this connector 13. The above-mentioned signal cable 14 is provided at the end with a connector 16 to be removably connected to the video processor 4. Also, the cable 15 is provided at the end with a connector 17 to be removably connected to the bending motor controlling apparatus 6.

The above-mentioned operating part 11 is provided with an air and water feeding button 18, a sucking button 19, a bending operation switch 29 and a speed setting switch 21 as a set speed switching instructing means.

Figure 1:
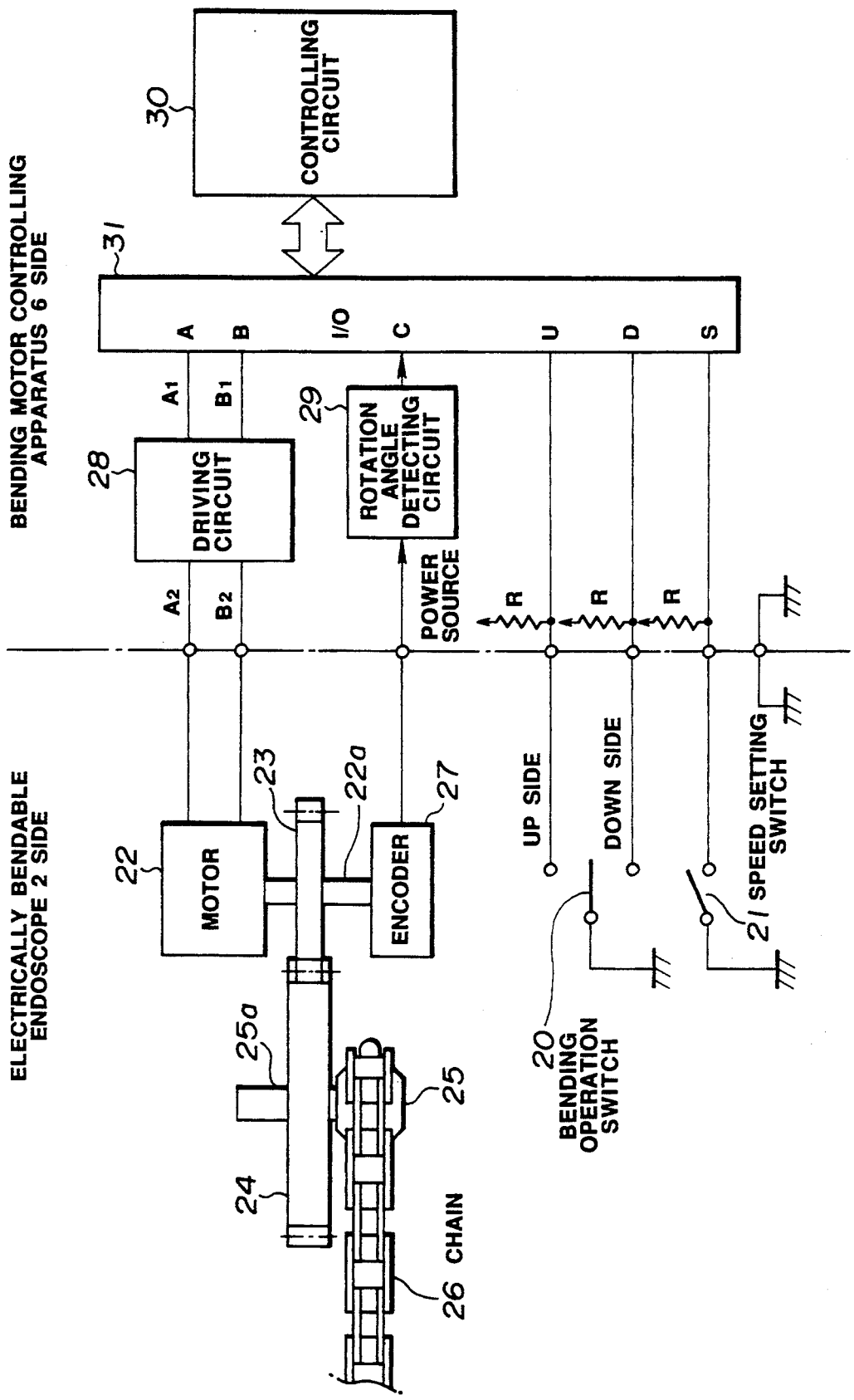
FIGS. 1 to 6 relate to the first embodiment of the present invention.

FIG. 1 shows an electric connection of the electrically bendable endoscope 2 and bending operation motor controlling apparatus 6 with each other and a part of the bending mechanism. The operating part 11 of this electrically bendable endoscope 2 is internally provided, for example, with a DC motor 22 as a driving part for bending the bendable part 8 and has a driving gear 23 secured midway on the rotary shaft 22a of the motor 22. A driven gear 24 meshing with this driving gear 23 is secured to a shaft 25a of a sprocket 25 with which a chain 26 is rotatably engaged. Two wires, not illustrated, are connected at the ends on one side to this chain 26 by a connecting member, not illustrated, and are inserted on the other end side through a plurality of rotatably combined articulate frames, not illustrated, and the respective wires are fixed, respectively, to the articulate frames on the tip part side. The wires are fixed at the other ends to the above-mentioned tip part 9 and are pulled and relaxed so that the above-mentioned bendable part 8 may be bent.

An absolute type encoder 27 is fixed on the tip part side of the rotary shaft 22a of the motor 22 so that the rotation angle of this motor 22 may be detected.

The bending motor controlling apparatus 6 comprises a driving circuit 28 as a driving means driving the above-mentioned motor 22, a rotation angle detecting circuit 29 converting the output signal from the above-mentioned encoder 27 to angle data which are output, a controlling circuit 30 as a controlling means for controlling the bending operation and bending speed and an input and output port (abbreviated as an I/O hereinafter) 31 interposed between the above-mentioned driving circuit 28, rotation angle detecting circuit 29, bending operation switch 20 and speed setting switch 21 and the controlling circuit 30 and intermediating between the input and output of the signal. The controlling circuit 30 and I/O 31 are connected between them through a bus line. The above-mentioned bending operation switch 20 is a switch for bending the above-mentioned bendable part 8 in the up or down direction. While its common terminal is grounded, its up terminal is connected to the terminal U of the I/O 31. A resistor R connected at one end to a power source is connected at the other end to the up terminal of the bending operation switch 20. The down terminal of the bending operation switch 20 is connected to the terminal D of the I/O. The resistor R connected at one end to the power source is connected at the other end to the down terminal of the bending operation switch 20. Also, the speed setting switch 21 is grounded at one end and is connected at the other end to the terminal S of the I/O 31. The resistor R connected at one end to the power source is connected at the other end to the speed setting switch 21 at the other end.

The above-mentioned driving circuit 28 is formed, for example, of a CPU or the like and outputs a controlling signal through the terminals A and B of the I/O 31. On the other hand, the rotation angle detecting circuit 29 outputs angle data to the controlling circuit 30 through the terminal C of the I/O 31.

The above-mentioned controlling circuit 30 controls the driving circuit 28 through the I/O 31 in response to the operation of the bending operation switch 20 and controls the bending driving/stopping and bending direction of the abovementioned bendable part 8. Also, the controlling circuit 30 converts the angle data of the rotation angle detecting circuit 29 to speed data corresponding to the bending speed (or the rotating speed of the motor 22) of the bendable part, and always monitors the bending speed of the bendable part 8 and controls the bending speed of the bendable part 8 in response to the operation of the speed setting switch 21.

Figure 3:
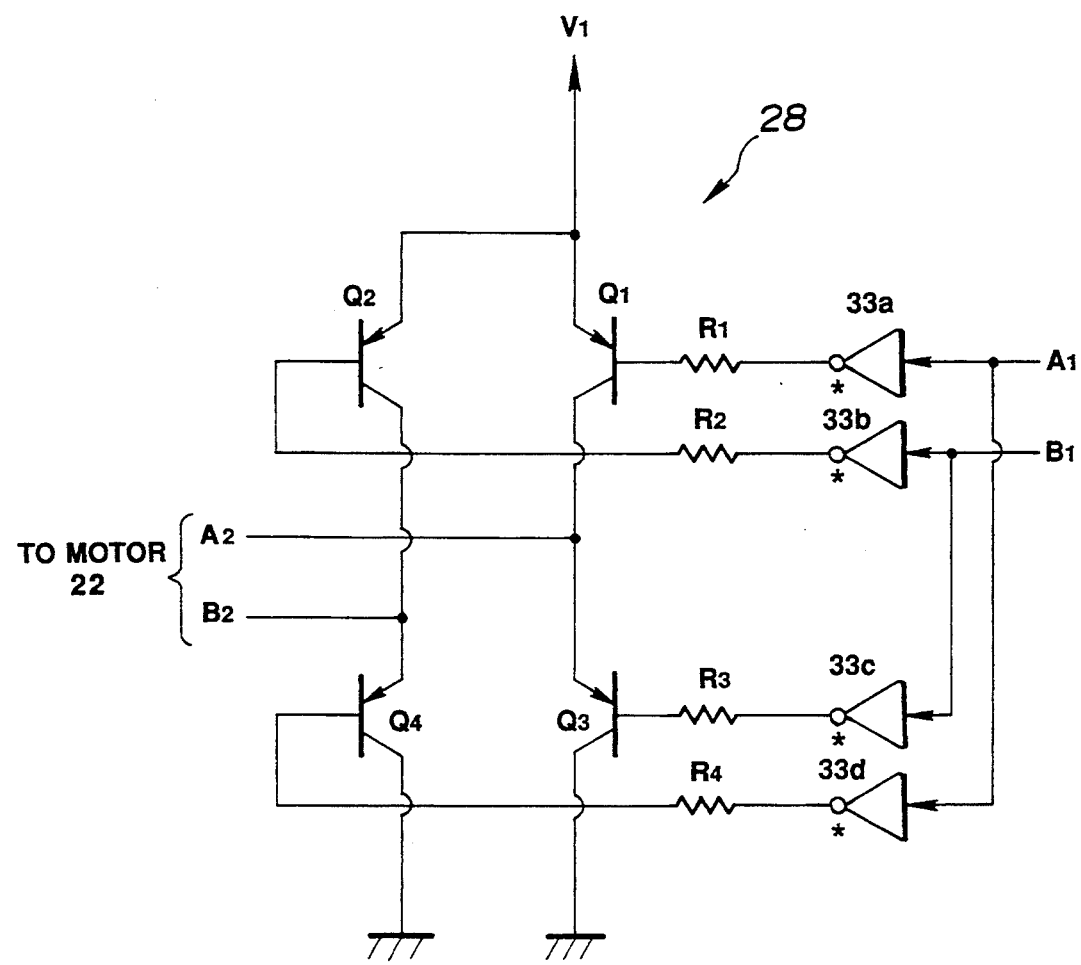

FIG. 3 shows an example of the driving circuit 28. In this driving circuit 28, in response to the respective output states of the terminals A and B of the I/O 31 indicated by the controlling circuit 30, the output signal to the motor 22 is switched to drive/stop the motor 22 or control the rotating direction. Open collector outputs inverters 33a and 33d input a controlling signal A1 of the controlling circuit 30 output by the terminal A of the I/O 31 and control transistors Q1 and Q4 to be on/off, respectively, through resistors R1 and R4 and the bases of the transistors Q1 and Q4. (In the drawing, the mark * represents an open collector output.) Open collector output inverters 33b and 33c input a controlling signal B1 of the controlling circuit 28 output by the terminal B of the I/O 31 and control transistors Q2 and Q3 to be on/off respectively through resistors R2 and R3 and the bases of the transistors Q2 and Q3. A power source V is connected to the respective emitters of the transistors Q1 and Q2. The emitter of the transistor Q3 and the negative terminal (A2 in the drawing) of the motor 22 are connected to the collector of the transistor Q1. Also, the emitter of the transistor Q4 and the positive terminal (B2 in the drawing) of the motor 22 are connected to the collector of the transistor Q2. The respective collectors of the transistors Q3 and Q4 are grounded.

In this embodiment, for the brevity of the explanation, the bending directions are limited to be only the up and down directions but may be four directions with the addition of the right and left directions. In such case, another separate system of such bending mechanism as of the chain 26 and gear, the motor 22 and bending operation switch 20 must also be provided.

Figure 4:
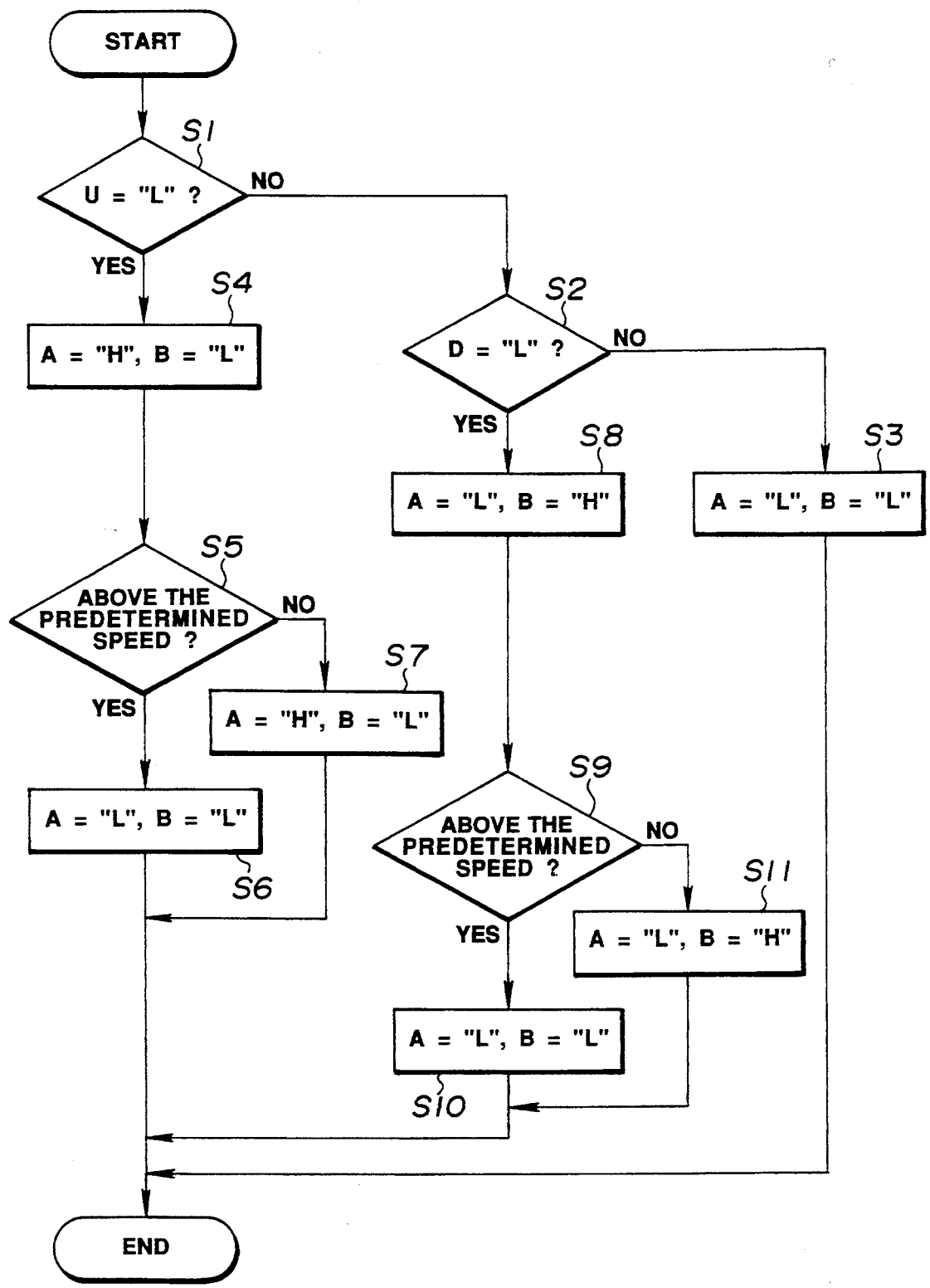

The operation of this embodiment shall be explained with reference to the charts in FIGS. 4 to 6.

When the power source of the bending motor controlling apparatus 6 is first switched on, the terminals D and U of the I/O 31 will become high ("H") and the controlling circuit 30 will judge the bendable part to be stationary and will instruct the terminals A and B of the I/O 31 to respectively output low ("L") signals. The transistors Q1 to Q4 will become all off and the bendable part 8 will remain stationary.

When the bending operation switch 20 is operated in the up direction, the terminal U of the I/O 31 will become low and the terminal D will become high and, through the judgment in the step S1, in the step S4, the controlling circuit 30 will instruct the terminal A of the I/O 31 to output a high signal and the terminal B to output a low signal. At this time, the transistors Q1 and Q2 will be on and, in the motor 22, the current will flow through the motor 22 in the direction from A2 to B2 in the drawing. Thus, the motor 22 will rotate in the up direction. By this rotation, the motor 22 tows the chain 26 and the above-mentioned wire through the driving gear 23, driven gear 24 and sprocket 25 and the bendable part 8 bends in the up direction. On the other hand, the rotation angle detecting circuit 29 converts the output pulses detected by the encoder 27 to angle data and outputs them to the controlling circuit 30 through the terminal C of the I/O 31. The controlling circuit 30 converts the above-mentioned angle data to speed data showing the bending speed of the bendable part 8. In the step S5, it is judged whether or not the value of these speed data is above a predetermined value, that is, whether or not the bending speed is above the later described predetermined speed. In the case of YES, in the step S6, the controlling circuit 30 will make both terminals A and B of the I/O 31 low and will make no electric current flow through the motor 22. In the case of NO, that is, if below the predetermined speed, in the step S7, the controlling circuit 30 will instruct the terminal A of the I/O 31 to output a high signal and the terminal B to output a low signal to continue the rotation of the motor 22 in the up direction. Thus, by a kind of PWM (Pulse Width Modulation) control, the motor 22 always rotates at a fixed speed.

When the bending operation switch 20 is operated in the down direction, the terminal U of the I/O 31 will become high and the terminal D will become low and, through the steps S1 and S2, in the step S8, the controlling circuit 30 will instruct the terminal A of the I/O 31 to output a low signal and the terminal B to output a high signal. At this time, the transistors Q2 and Q3 will be on, the current will flow in the direction from B2 to A2 in the drawing through the motor 22 which will rotate in the down direction. Then, by this rotation, the motor 22 will tow the chain 25 and the above-mentioned wire through the driving gear 23, driven gear 24 and sprocket 25 and the bendable part 8 will bend in the down direction. On the other hand, in the step S9, the same as is mentioned above, on the basis of the speed data, the controlling circuit 30 will judge whether the value of these speed data is above a predetermined value or not, that is, whether the bending speed is above a predetermined speed or not. In the case of YES, in the step S10, the controlling circuit 30 will make the terminals A and B of the I/O 31 both low and will not make the current flow through the motor 22. In the case of NO, that is, if below the predetermined speed, the controlling circuit 30 will instruct the terminal A of the I/O 31 to output a low signal and the terminal B to output a high signal to continue the rotation in the down direction of the motor 22. Thus, by a kind of PWM control, the motor 22 rotates always at a fixed speed.

In case the bending operation switch 20 is not operated, that is, in case the switch is neutral, the terminals U and D of the I/O 31 will be high and therefore, through the steps S1 and S2, in the step S3, the controlling circuit 30 will set both terminals A and B of the I/O 31 to be low and the transistors Q1 to Q4 will be all off. Therefore, no current will flow through the motor 22 which will remain stopped and the bendable part 8 will remain stationary.

Figure 5:
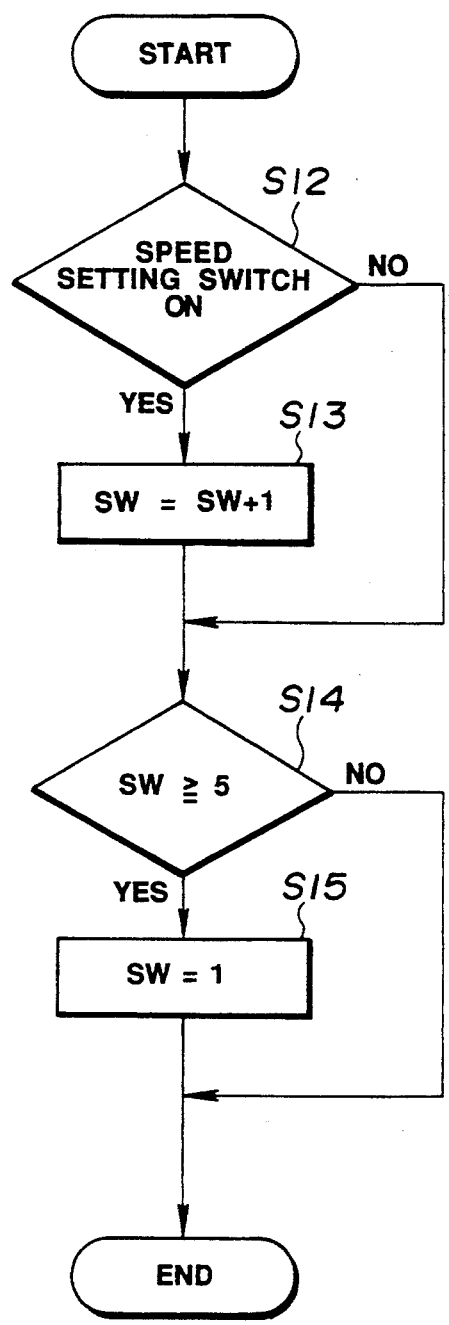
Figure 6:
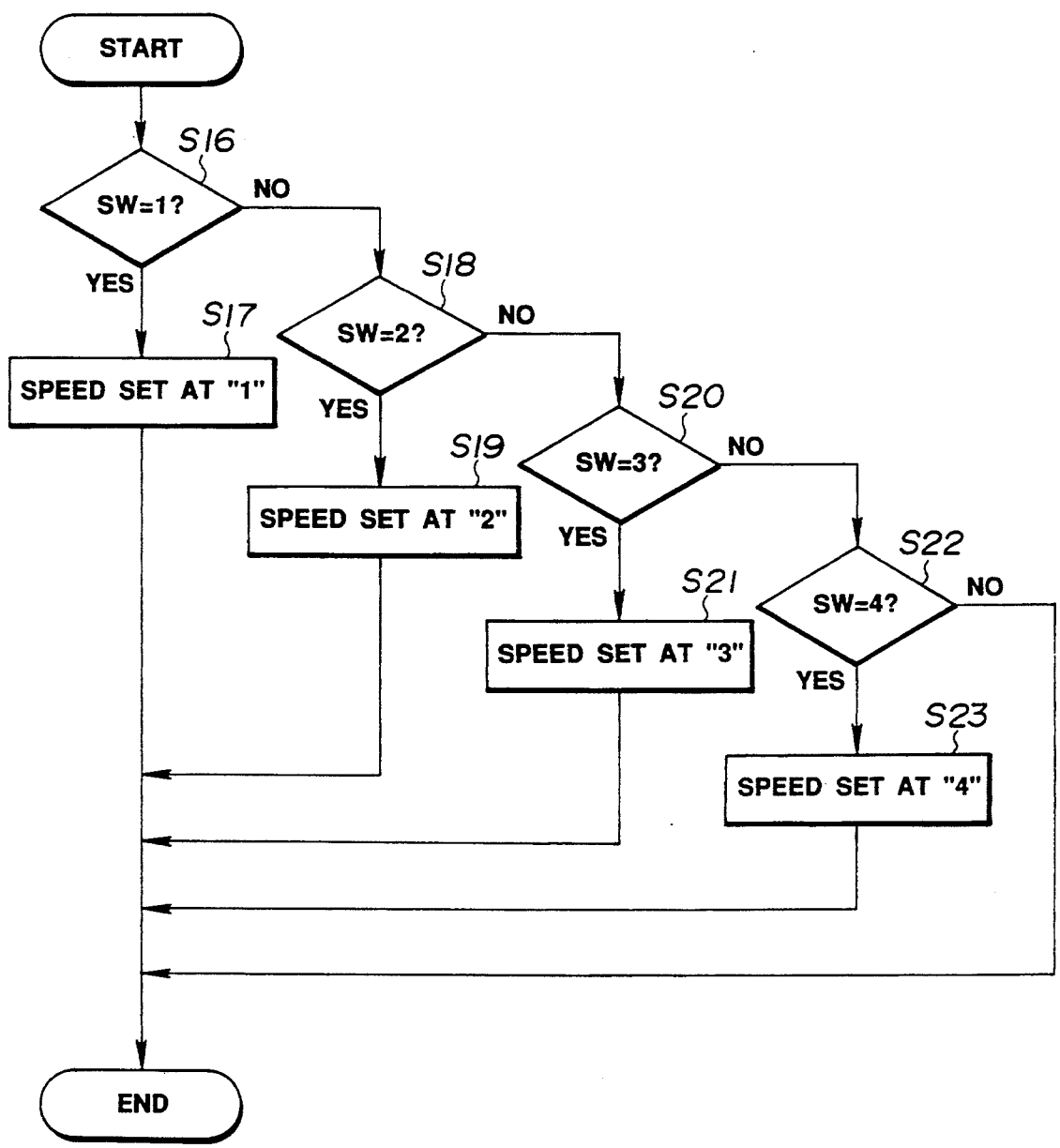

Now, FIGS. 5 and 6 are flow charts showing the procedures of the controlling circuit 30 in case the speed setting switch 21 is operated.

When the power source of the bending motor controlling apparatus is switched on, the flag SW for setting the speed to be set within the controlling circuit 30 will be set first at "1". When the speed setting switch 21 is switched on in the step S12 in FIG. 5, in the step S13, the flag SW will have "1" added each time when it is switched on. When the speed setting switch 21 is not on, the flag SW will remain as it is until it is switched on next. In the step S14, it is judged whether the flag SW>5 When above "5" the flag SW will be returned again to "1" in the step S15. That is to say, the flag SW will have "1" added each time when the speed setting switch 21 is switched on and will be always "1" to "4".

When the flag SW is "1" in the step S16 in FIG. 6, the speed will be set at "1" in the step S17. The speed set here is a predetermined speed to be a judging reference in the steps S5 and S9 in the above-mentioned FIG. 4. When the fag SW is "2" in the step S18, the speed will be set at "2" in the step S19. When the flag SW is "3" in the step S20, the speed will be set at "3" in the step S21. When the flag SW is "4" in the step S22, the speed will be set at "4" in the step S23.

In this embodiment, the motor 22 can be driven at a predetermined speed always set in response to the operation of the bending operation switch 20 and the bendable part 8 can be bent at a fixed speed. Therefore, the bending operation can be made at a fixed bending speed, and even a beginner can safely make the bending operation at rest.

Also, in this embodiment, a predetermined speed set within the controlling circuit 30 can be variably set by the operation of the speed setting switch 21 and the bending operation can be made at any one of the set bending speeds which can be determined steppedly. A mode of operating at a slow fixed bending speed by the operation of the speed setting switch 21 in case the load quickly becomes large in the bending operation can be set in advance to avoid an emergency and to keep the safety.

Further, in this embodiment, as the bendable part 8 is controlled by the controlling circuit 30 so as to remain stationary when the power source of the controlling apparatus 6 is on, the bendable part can be prevented from moving unexpectedly to hurt the interior of a body cavity. Thus, in this embodiment, the bending operation is made safe even in such initial state as when the power source is switched on.

The bending operation may be made at a fixed bending speed without particularly requiring the speed setting switch 21.

Figure 7:
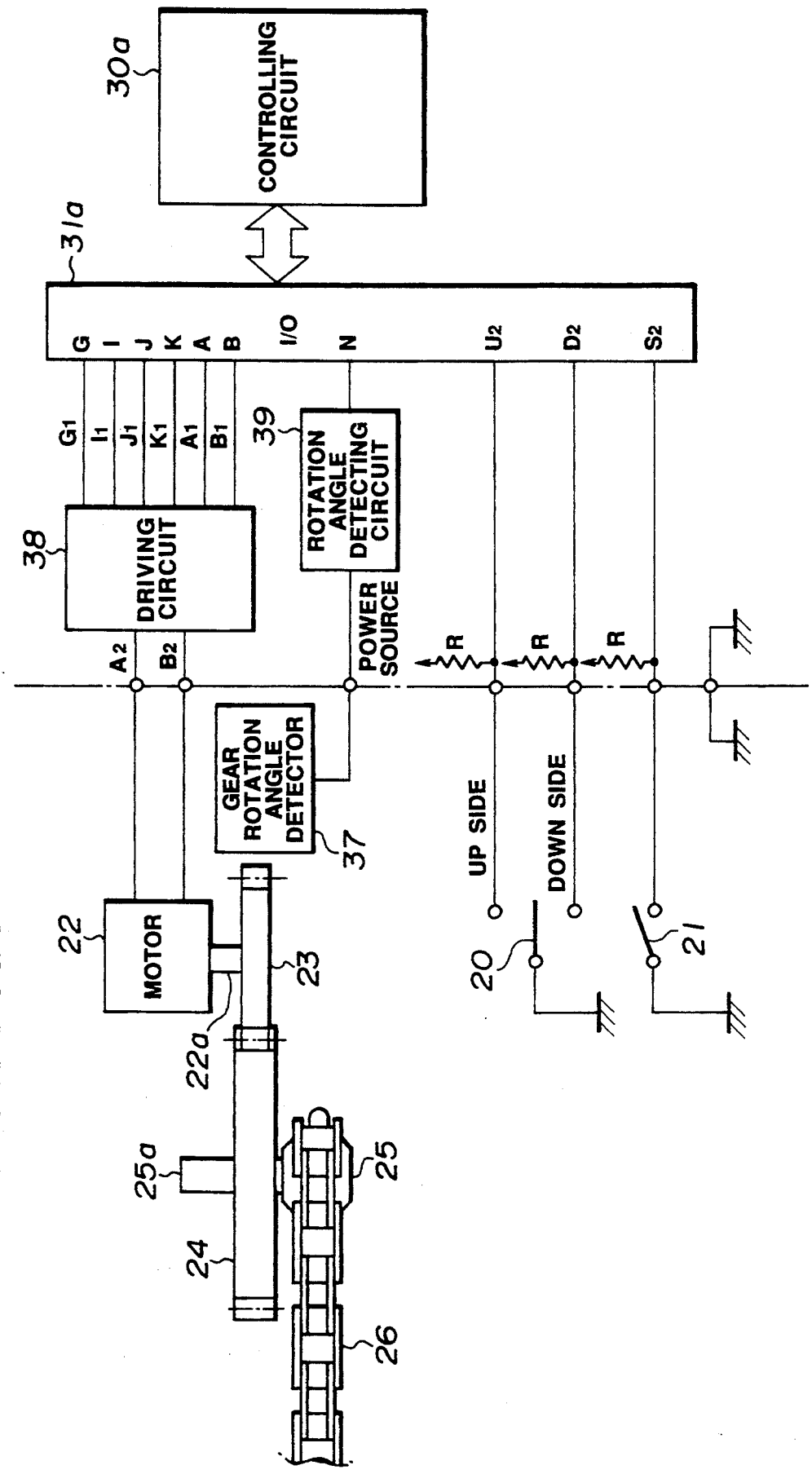
FIGS. 7 to 11 relate to the second embodiment of the present invention.
Figure 11:
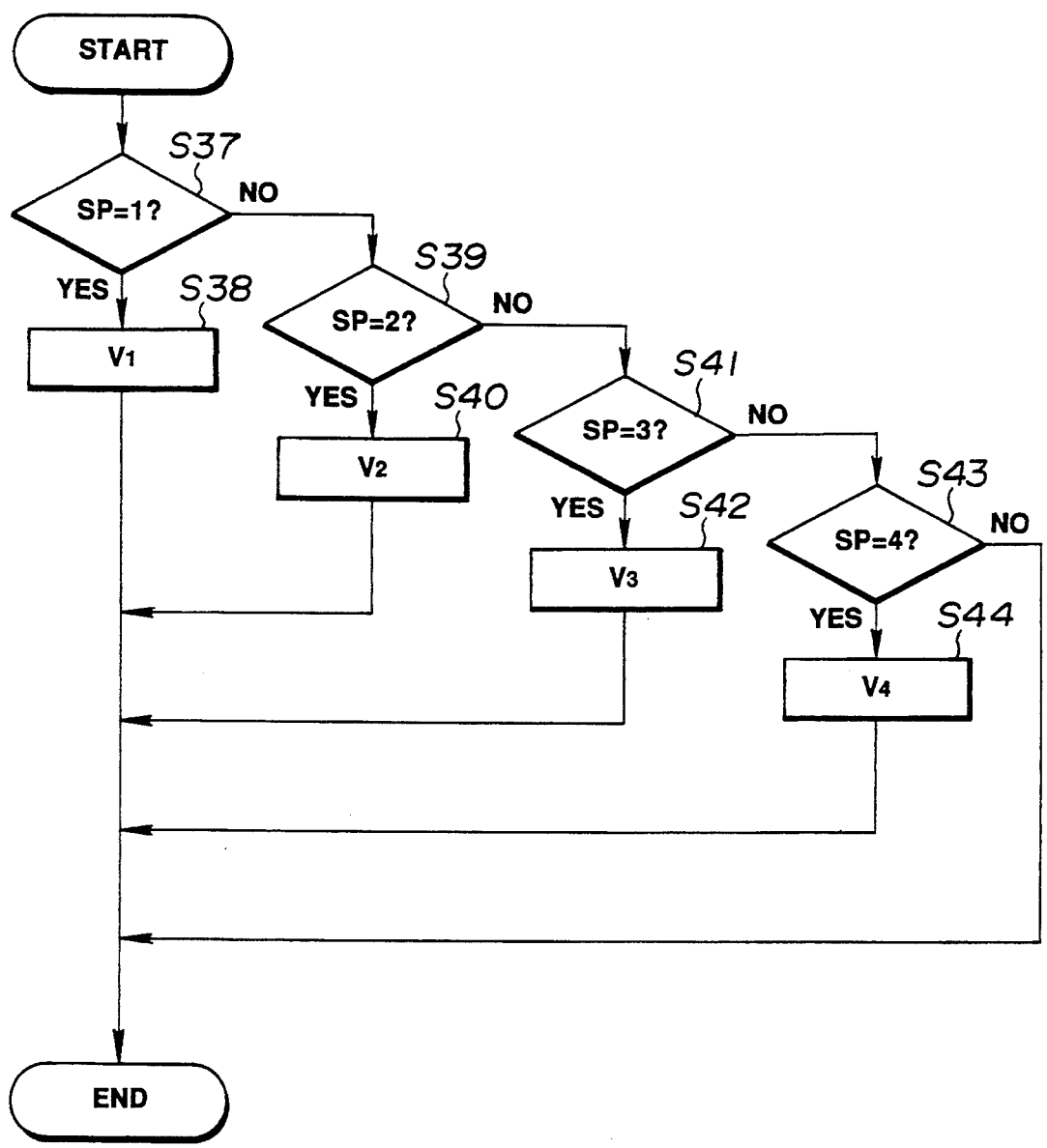

FIGS. 7 and 11 relate to the second embodiment of the present invention. The second embodiment shall be explained as follows:

In the electrically bendable endoscope apparatus of this second embodiment, a fixed bending speed is obtained by steppedly switching the voltage. As shown in FIG. 7, this embodiment is provided with an electrically bendable endoscope 40 having a gear rotating angle detector 37 which is an adjacent sensor for detecting the rotating angle of the motor 22 in place of the above-mentioned encoder 27 of the electrically bendable endoscope 2 of the first embodiment. Also, this embodiment is provided with a driving circuit 38, rotating angle detecting circuit 39, I/O 31a and controlling circuit 30a in place of the driving circuit 28, rotating angle detecting circuit 29, I/O 31 and controlling circuit 30 of the first embodiment. The I/O 31a and controlling circuit 30a are of substantially the same formations as of the above-mentioned I/O 31 and controlling circuit 30. The other same formations and operations as of the first embodiment shall bear the same reference numerals and shall not be explained here.

The above-mentioned gear rotating angle detector 37 consists, for example, of a light receiving and emitting device, is arranged near the-above-mentioned driving gear 23 and outputs a pulse signal proportional to the number of revolutions of the motor 22 from the rotation of the gear of the driving gear 23. The above-mentioned rotating angle detecting circuit 39 converts the detecting signal of the gear rotating angle detector 37 to angle data and outputs the angle data to the above-mentioned controlling circuit 30 through the terminal N of the I/O 31a. The controlling circuit 30a sets and outputs controlling signals for setting the speed to the terminals G, I, J and K of the I/O 31a. The above-mentioned driving circuit 38 switches the voltage applied to the motor 22 by the above-mentioned controlling signals.

Figure 8:
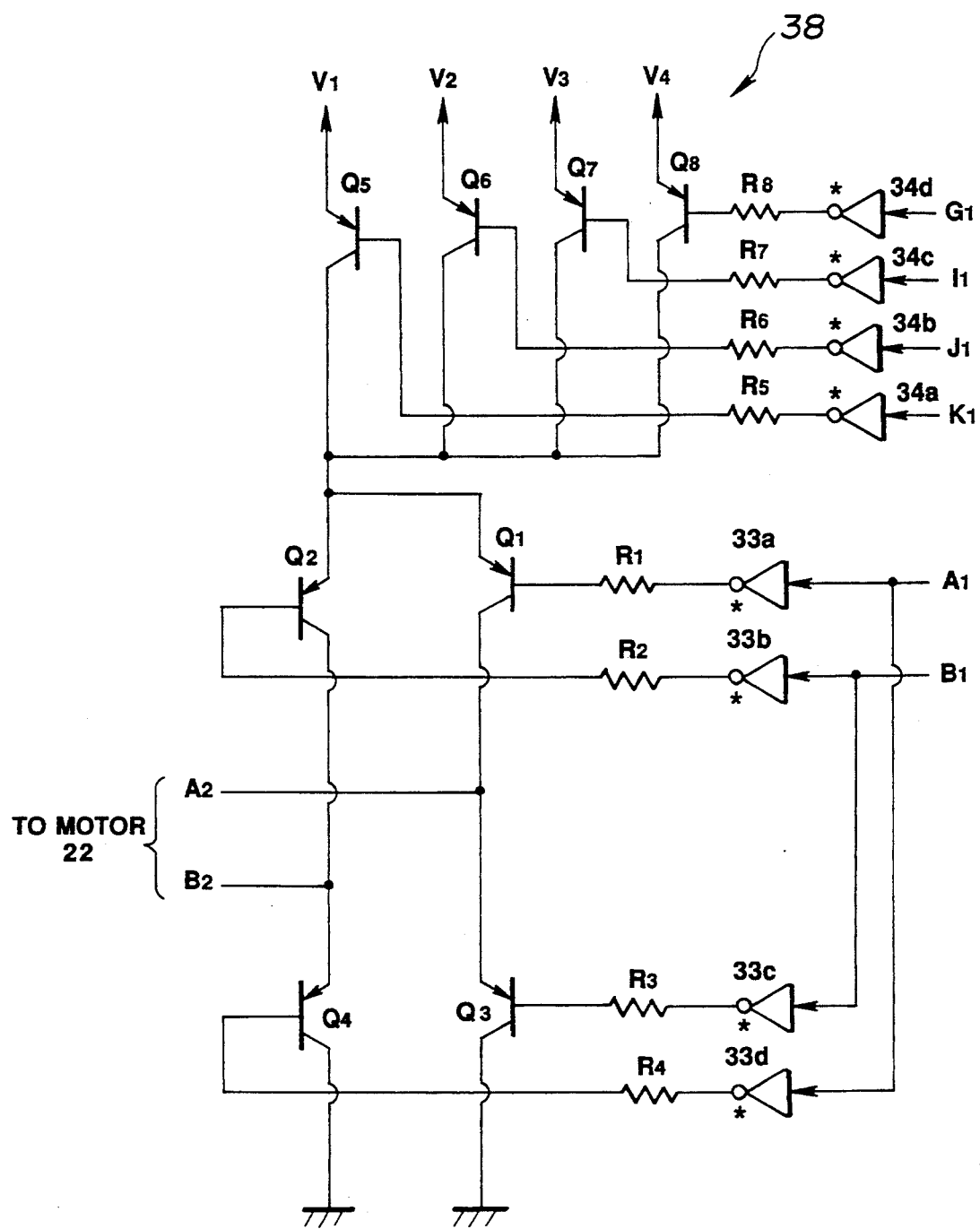

As shown in FIG. 8, the driving circuit 38 is of a formation that, according to the setting of the controlling signals output respectively from the terminals K, J, I and G of the I/O 31a, one of different voltages V1, V2, V3 and V4 is selectively applied to the motor 22 in place of the formation that the voltage V of the above-mentioned driving circuit 28 is applied. Therefore, the above-mentioned bendable part 8 is to be bent at any one of the predetermined speeds set steppedly. The terminals K, J, I and G of the I/O 31 output respectively controlling signals K1, J1, I1 and G1 in response to the instruction from the controlling circuit 30 and respectively control transistors Q5, Q6, Q7 and Q8 to be on/off respectively through open collector inverters 34a, 34b, 34c and 34d, resistors R5, R6, R7 and R8 and the bases of the transistors Q5, Q6, Q7 and Q8. Power sources V1, V2, V3 and V4 of different voltage values are connected to the respective emitters of the transistors Q5, Q6, Q7 and Q8. The respective collectors of the transistors Q5, Q6, Q7 and Q8 are connected in common to the emitters of the above-mentioned transistors Q1 and Q2. The above-mentioned bending operation switch 20 has its up terminal connected to the terminal U2 of the I/O 31a and the down terminal connected to the terminal D2 of the I/O 31a. The above-mentioned speed setting switch 21 is connected at the other end to the terminal S2 of the I/O 31a.

The operation of this embodiment shall be explained with reference to FIGS. 9 to 11.

When the power source of the bending motor controlling apparatus 41 is first switched on, the terminals D2 and U2 will respectively become high ("H") and the controlling circuit 30a will judge the bendable part to be stationary and will instruct the terminals A and B of the I/O 31a to respectively output low ("L") signals. The transistors Q1 to Q4 will be all off. The bendable part 8 will remain stationary. At the same time, in the controlling circuit 30a, the flag SP1 will be set. The terminal K of the I/O 31a will become high and the transistor Q5 will be on. By the way, the voltage values will be V1<V2<V3<V4.

When the bending operation switch 20 is operated in the up direction, the terminal U2 of the I/O 31a will become low and the terminal D2 will become high. In FIG. 9, through the step S25, in the step S28, the controlling circuit 30a will instruct the terminal A to output a high signal and the terminal B to output a low signal. At this time, the transistor Q5 will be already on, the transistors Q1 and Q4 will become on, the voltage V1 will be applied to the motor 22, the current will flow in the direction from A2 to B2 and the motor 22 will rotate in the up direction. By this rotation, the motor 22 will tow the chain 26 and the above-mentioned wire through the driving gear 23, driven gear 24 and sprocket 25 and the bendable part 8 will bend in the up direction.

Figure 10:
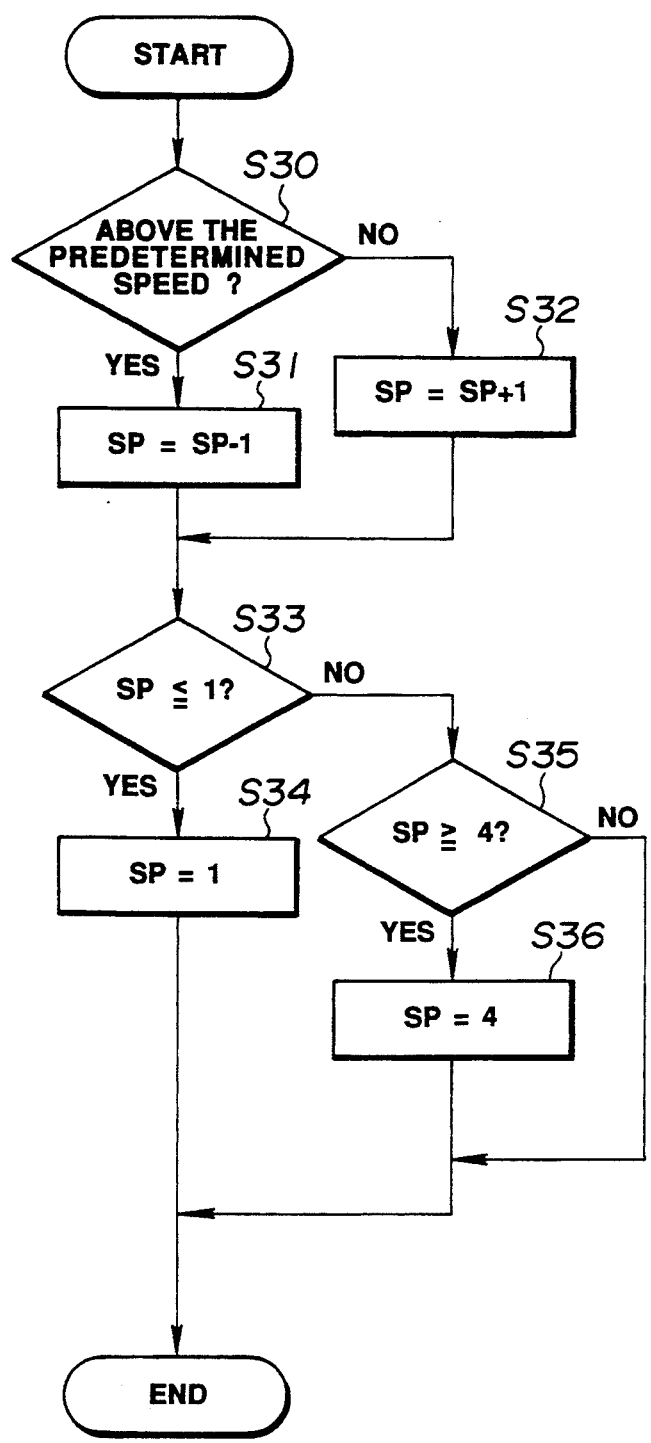

FIGS. 10 and 11 are flow charts showing the procedures for controlling the speed.

The above-mentioned rotating angle detecting circuit 39 converts the output pulses detected by the gear rotating angle detector 37 to angle data and outputs the angle data to the controlling circuit 30a through the terminal N of the I/O 31a. The controlling circuit 30a converts the above-mentioned angle data to speed data showing the bending speed of the bendable part 8. In the step S30 in FIG. 10, it is judged whether or not the value of these speed data is above the value of a predetermined speed, that is, whether or not the bending speed is above the predetermined speed. In case above the predetermined speed (YES), in the step S31, the flag SP set within the controlling circuit 30a will be subtracted by "1". If below the predetermined speed, in the step S32, the flag SP will be added by "1". By the way, in the step S33, it is judged whether or not the flag SP≦1. When below "1" in the step S34, the flag SP will be returned to "1" again. When above "1" in the step S35, it will be judged whether the flag SP≦1 or not. When above "4", in the step S36, the flag SP will be returned to "4" again That is to say, so as to keep the predetermined speed, the flag SP will be added or subtracted by "1" and will be set always at "1" to "4".

In the step S37 in FIG. 11, when the flag SP is "1" the controlling circuit 30a will make the terminal K of the I/O 31a high, will make the terminals J, I and G respectively low and will switch on only the transistor Q5. In the step S38, the power source V1 is fed to the motor 22 through the respective transistors. In the step S39 in FIG. 11, when the flag SP is "2" the controlling circuit 30a will make the terminal J of the I/O 31a high, will make the terminals K, I and G respectively low and will switch on only the transistor Q. In the step S40, the power source V2 will be fed to the motor 22 through the respective transistors. In the step S41 in FIG. 11, when the flag SP is "3" the controlling circuit 30a will make the terminal I of the I/O 31a high, will make the terminals K, J and G respectively low and will switch on only the transistor Q7. In the step S42, the power source V3 will be fed to the motor 22 through the respective transistors. In the step S43 in FIG. 11, when the flag SP is "4" the controlling circuit 30a will make the terminal G of the I/O 31a high, will make the terminals K, J and I respectively low and will switch on only the transistor Q8. In the step S44, the power source V4 will be fed to the motor 22 through the respective transistors.

Thus, by the respective steps in the above-mentioned FIGS. 10 and 11, the controlling circuit 30a will reduce the voltage applied to the motor 22 if the bending speed is above the predetermined speed and will elevate the voltage applied to the motor 22 if below the predetermined speed. The controlling circuit 30a controls the bending speed of the bendable part to be fixed.

Now, when the bending operation switch 20 is operated in the down direction, the terminal U2 of the I/O 31a will become high and the terminal D2 will become low. Through the steps S25 and S26 in FIG. 9, in the step S29, the controlling circuit 30a will instruct the terminal A of the I/O 31 to output a low signal and the terminal B to output a high signal. At this time, the transistors Q2 and Q3 will be on, the current will flow to the motor 22 in the direction from B2 to A2 in the drawing and the motor 22 will rotate in the down direction. By its rotation, the motor 22 will tow the chain 26 and the above-mentioned wire through the driving gear 23, driven gear 24 and sprocket 25 and the bendable part 8 will bend in the down direction. On the other hand, in the step S30 in FIG. 10, on the basis of the speed data the same as in the above, the controlling circuit 30a will judge whether or not the value of these speed data is above the predetermined value, that is, whether or not the bending speed is above the predetermined speed. By the respective steps in FIGS. 10 and 11, the controlling circuit 30a will reduce the voltage applied to the motor 22 if the bending speed is above the predetermined speed and will elevate the voltage applied to the motor 22 if below the predetermined speed. The controlling circuit 30a controls the bending speed of the bendable part 8 so as to be fixed.

Figure 9:
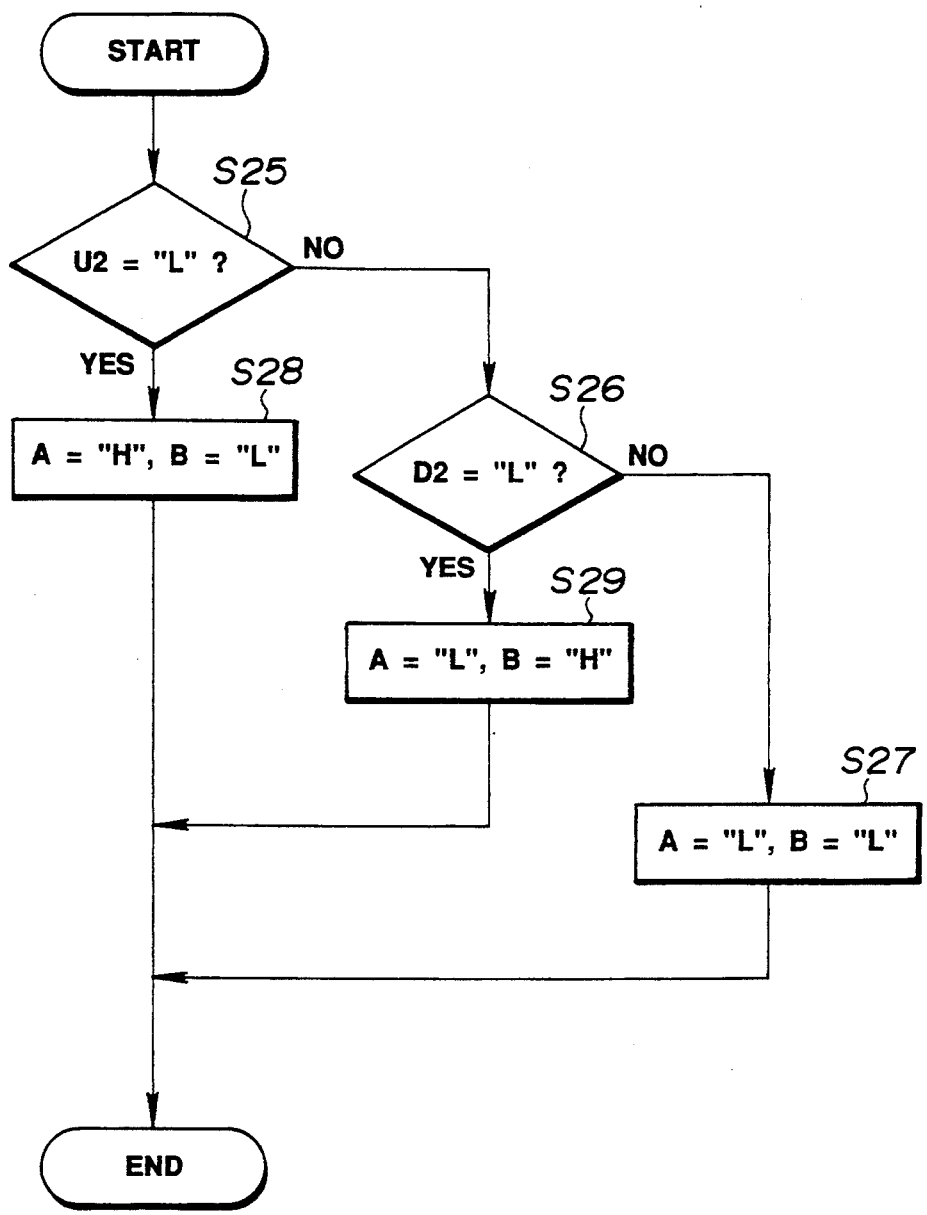

In case the bending operation switch 20 is not operated, that is, in case the switch 20 is neutral, the terminals U2 and D2 of the I/O 31a will be high and therefore, through the steps S25 and S26 in FIG. 9, in the step S27, the controlling circuit 30a will set the outputs of the terminals A and B of the I/O 31 to be both low and the transistors Q1 to Q4 will all be off. Therefore, no current will flow through the motor 22 which will stop and the bendable part 8 will remain stationary.

In this embodiment, the motor 22 is driven at a predetermined speed set always in response to the operation of the bending operation switch 20 and the bendable part 8 can be bent at a fixed speed. Therefore, the bending operation can be made at a fixed bending speed, and even a beginner can safely make the bending operation at rest.

The operation of the speed setting switch is the same as in the first embodiment. The predetermined speed described in the second embodiment is set as in the first embodiment. The speed setting switch 21 is not particularly required and the bending operation may be made at a fixed bending speed.

In this embodiment, it is judged whether or not the above-mentioned speed data obtained for the predetermined speed set within the controlling circuit 30a are above the predetermined speed, the flag SP is added or subtracted, the voltage applied to the motor 22 is switched steppedly and therefore the motor 22 can be driven always at a fixed rotating speed. Therefore, unless the speed setting switch 21 is switched, even if the load fluctuates, the bending operation will be able to be made at a fixed bending speed and at rest.

The other formations, operations and effects are the same as in the first embodiment and shall not be explained here.

The third embodiment shall be explained in the following FIGS. 12 to 15 relating to the third embodiment.

The third embodiment is different from the first embodiment only in the formation of the bending motor controlling apparatus. The other formations are the same as in the first embodiment. Therefore, only the different formations shall be explained and the same formations and operations as in the first embodiment shall bear the same reference numerals and shall not be explained here.

Figure 12:
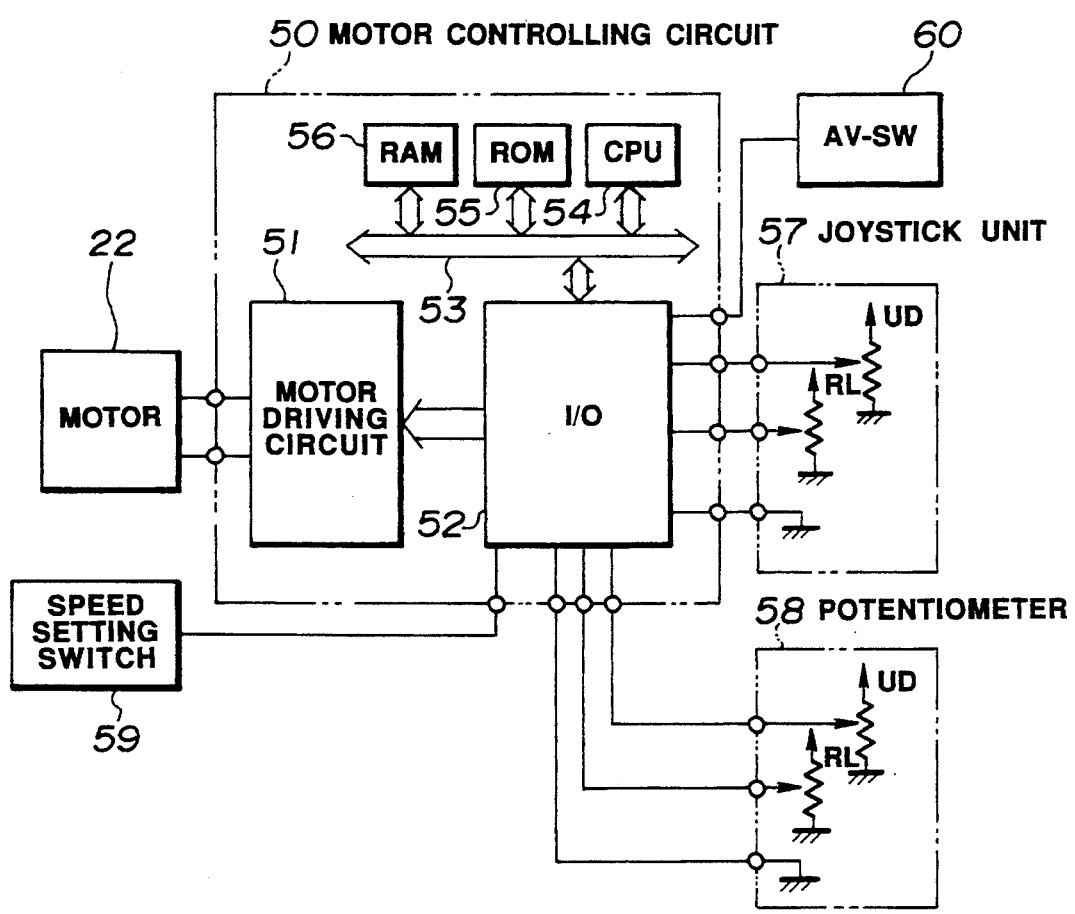
FIGS. 12 to 13 relate to the third embodiment of the present invention.

As shown in FIG. 12, in a motor controlling circuit 50, a motor driving circuit 51 feeding a driving current to the motor 22 is provided and is connected to a CPU 54 controlling the bending driving system through an I/O 52 and bus line 53. Also, a ROM 55 housing programs or the like and a RAM 56 housing data or the like are provided on the bus line 53. To an I/O 52 are connected a joystick unit 57, a potentiometer 58 for detecting a bending angle and as an angle detecting means, a speed setting switch 59 and an angle vibrating (abbreviated as AV hereinafter) switch 60. The joystick unit 57 is provided with potentiometers respectively corresponding to the up and down direction (UD) and the right and left direction (RL).

Figure 13:
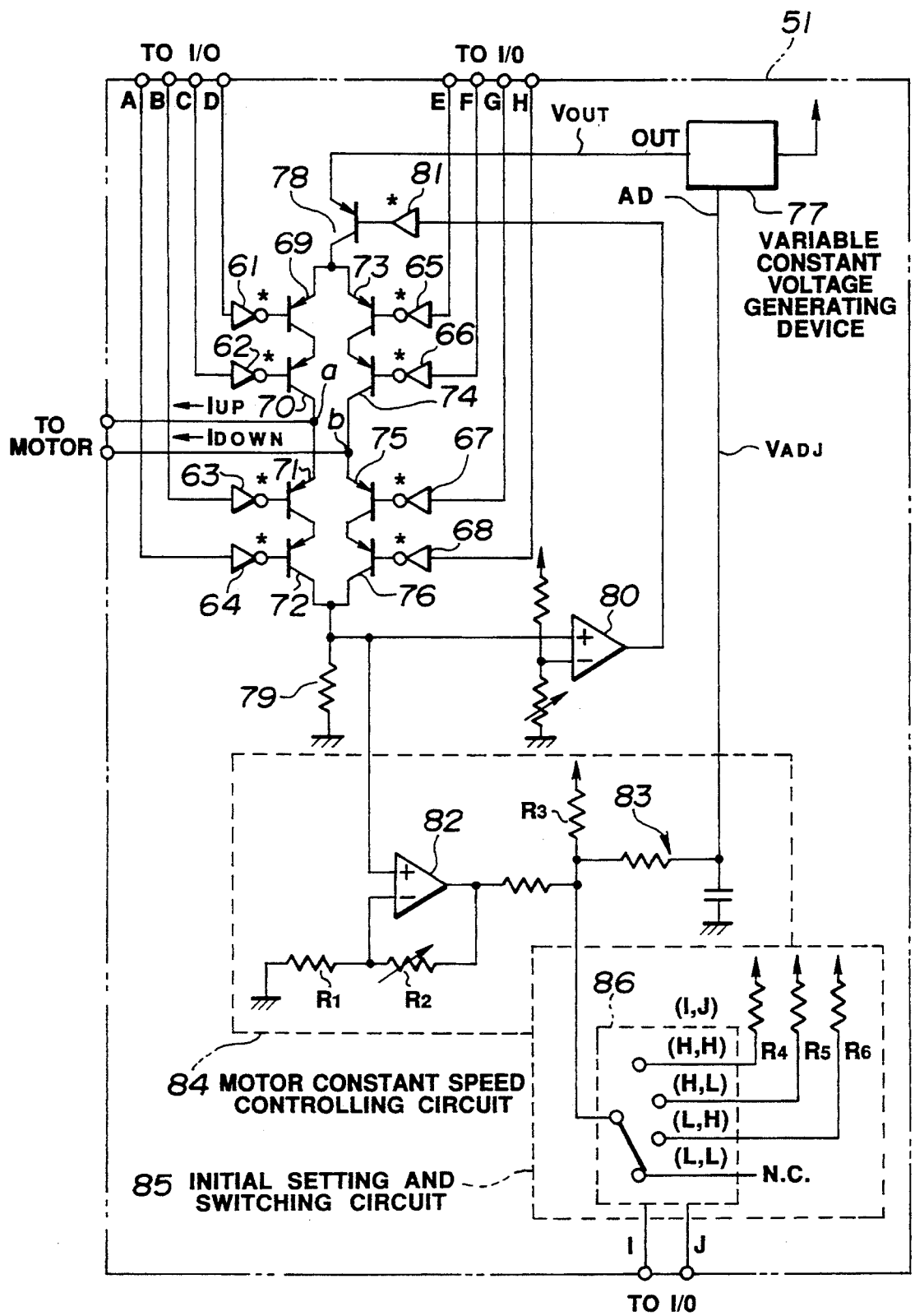

The above-mentioned motor driving circuit 51 is formed as shown in FIG. 13. For the brevity of the drawing, only the circuit in the up and down direction is shown, and the formation in the right and left direction is the same. This motor driving circuit 51 is provided with an H bridge circuit formed by connecting the bases of transistors 69 to 76, respectively, to inverters 61 to 68 of open collector outputs. The input terminals A to H of these inverters 61 to 68 are connected to the I/O 52. Terminals are provided at points a and b of the above-mentioned H bridge circuit and are connected to the motor 22. When a high level (mentioned as "H" hereinafter) is input into the inverters 61 to 68, the transistors will be on and the current will flow. That is, when a low level (mentioned as "L" hereinafter) is input into the terminals A, B, E and F and "H" is input into the terminals C, D, G and H, a current I UP in the up direction will flow through the motor 22. When "H" is input into A, B, E and F and "L" is input into C, D, G and H, a current I DOWN in the down direction will flow through the motor 22.

For the SFC (signal fault condition) countermeasures, that is, so that, even if one of the transistors shorts, there may be no misoperation, two inverters and transistors are provided.

On the current input side of the above-mentioned H bridge circuit, a variable constant voltage generating device 77 is provided as a current feeding source and is connected to the H bridge circuit through a transistor 78. The current output side of the H bridge circuit is connected to the ground (GND hereinafter) through a resistor 79. The H bridge circuit side of the resistor 79 is connected to a comparator 80. The output end of this comparator 80 is connected to the base of the above-mentioned transistor 78 through a buffer 81 of the open collector output. As a voltage responding to the current amount flowing through the above-mentioned H bridge circuit is generated at both ends of the resistor 79, the comparator 80 compares this voltage with a fixed set voltage. In case this voltage exceeds the set value, "H" will be output. Here, the transistor 78 is usually on. In case an excess current above a fixed amount flows through the H bridge circuit, the "H" will be input into the buffer 81, the transistor 78 will be off and the current will be interrupted.

A motor constant speed controlling circuit 84 as a controlling means consisting of an operational amplifier 82 and integrating circuit 83 is connected to the H bridge circuit side of the above-mentioned resistor 79. The variable constant voltage device 77 varies the output voltage V OUT in response to the input voltage V ADJ of an ADJ terminal. When the current flowing through the motor 31 becomes large, the voltage at both ends of the resistor 79 will also become large and the output voltage of the motor constant speed controlling circuit 84 will become large. In the DC motor, the larger the load, the larger the flowing current. Therefore, by varying the V ADJ in the motor constant speed controlling circuit 84, the output voltage V OUT of the variable constant voltage generating device 77 responding to the load will be obtained in the motor. Thereby, the drive can be controlled to rotate at a constant speed irrespective of the load of the motor.

The resistors R1, R2 and R3 within the above-mentioned motor constant speed controlling circuit 84 are resistances for setting the speed. An initial setting and switching circuit 85 as a speed setting and switching means is provided in parallel with the resistor R3. This initial setting and switching circuit 85 is provided with a switching switch 86 whose input terminals I and J are connected to the I/O 52. A signal responding to the setting of the speed setting switch 80 is to be input into the input terminals I and J. Four kinds of switching signals, for example, of (H,H), (H,L), (L,H) and (L,L) are input into (I,J) in response to the setting of the speed setting switch 80. Thereby, the switching switch 86 switches the resistors and selects and connects any of the R4, R5 and R6 in parallel with the R3 or connects nothing. Here, when (I,J) is (L,L), the initial set voltage of V ADJ will be the lowest and the initial set voltage will become higher in the order of (L,H), (H,L) and (H,H). That is, the initial set voltage will become higher in response to the speed of the initial set speed.

The other formations are the same as in the first embodiment.

The operation of the thus formed third embodiment shall be explained.

First of all, by setting the speed setting switch 59, the initial setting and switching circuit 75 switches the speed setting resistance in four steps. Then, following the flow chart shown in FIG. 14, in S50, the output voltage V JS output by the operation of the joystick unit 57 and the output voltage V PT of the bending angle detecting potentiometer 58 are compared with each other. If V JS>V PT, the process will proceed to S51 and, if V JS≦V PT, the process will proceed to S52. In S51, the electric current in the up direction flows through the motor 22. In S52, the electric current in the down direction flows through the motor 22.

Here, when the bending resistance becomes large and the load on the motor 22 becomes large, the speed of the motor 22 will tend to become low and the electric current flowing through the motor 22 will become large. As a result, the voltage generated in the resistance 79 will become high, the V ADJ of the variable constant voltage generating device 77 will become large by the control of the constant speed controlling circuit 84 and therefore the V OUT will also become large.

Thus, if the load on the motor 22 becomes large, the fed voltage will also become large and therefore, irrespective of the load on the motor 22, the motor 22 will rotate at a substantially constant speed set by the speed setting switch 59.

For brevity, only the operation in the up and down direction has been explained here, but the operation is also the same in the right and left directions.

The other operations and effects are the same as in the first embodiment.

By the way, in the third embodiment, the bending speed is set by the initial setting and switching circuit 85 and speed setting switch 59. However, as a modification of the third embodiment, the formation may exclude the initial setting and switching circuit 85 and speed setting switch 59. In such modification of the formation, the speed cannot be set so freely as in the third embodiment but the motor 22 can be rotated at a constant speed irrespective of the load on the motor 22 with a simpler formation.

Figure 14:
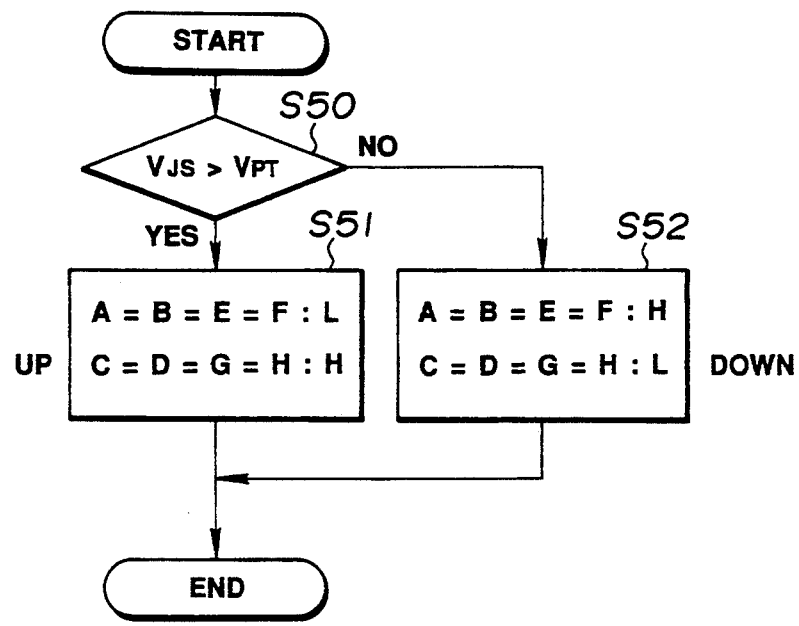
FIG. 14 is a flow chart showing the control of the motor driving.
Figure 15:
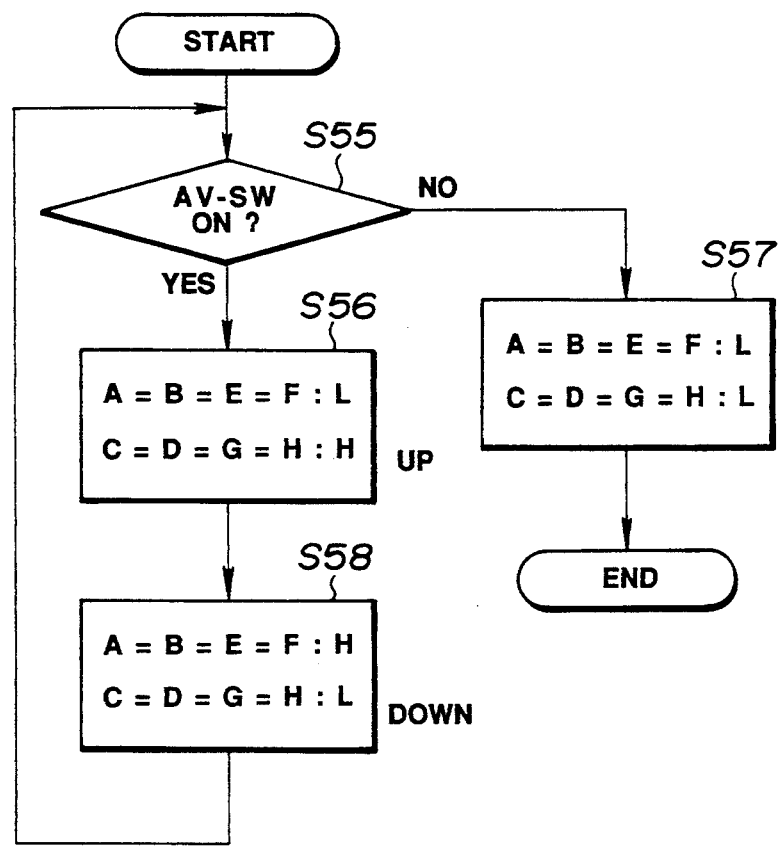
FIG. 15 is a flow chart for explaining an angle vibrating operation.

In the case of the AV operation by using the formation of the above-mentioned third embodiment or the modification of the third embodiment, as shown in FIG. 15, in S55, it is judged whether or not the AV switch 60 is on. If YES, the process will proceed to S56. If NO, the process will proceed to S57. In S56, for example, the current is made to flow in the up direction and then in the down direction and this operation is repeatedly continued. The process returns to S55. Therefore, this operation is continued until the AV switch 60 is off. In S55, it is judged to be NO, that is, the AV switch 60 is off. The process proceeds to S58 where A to H are made "L", the current is stopped and the control shown in FIG. 14 is returned.

The fourth embodiment shall be explained in the following.

Figure 16:
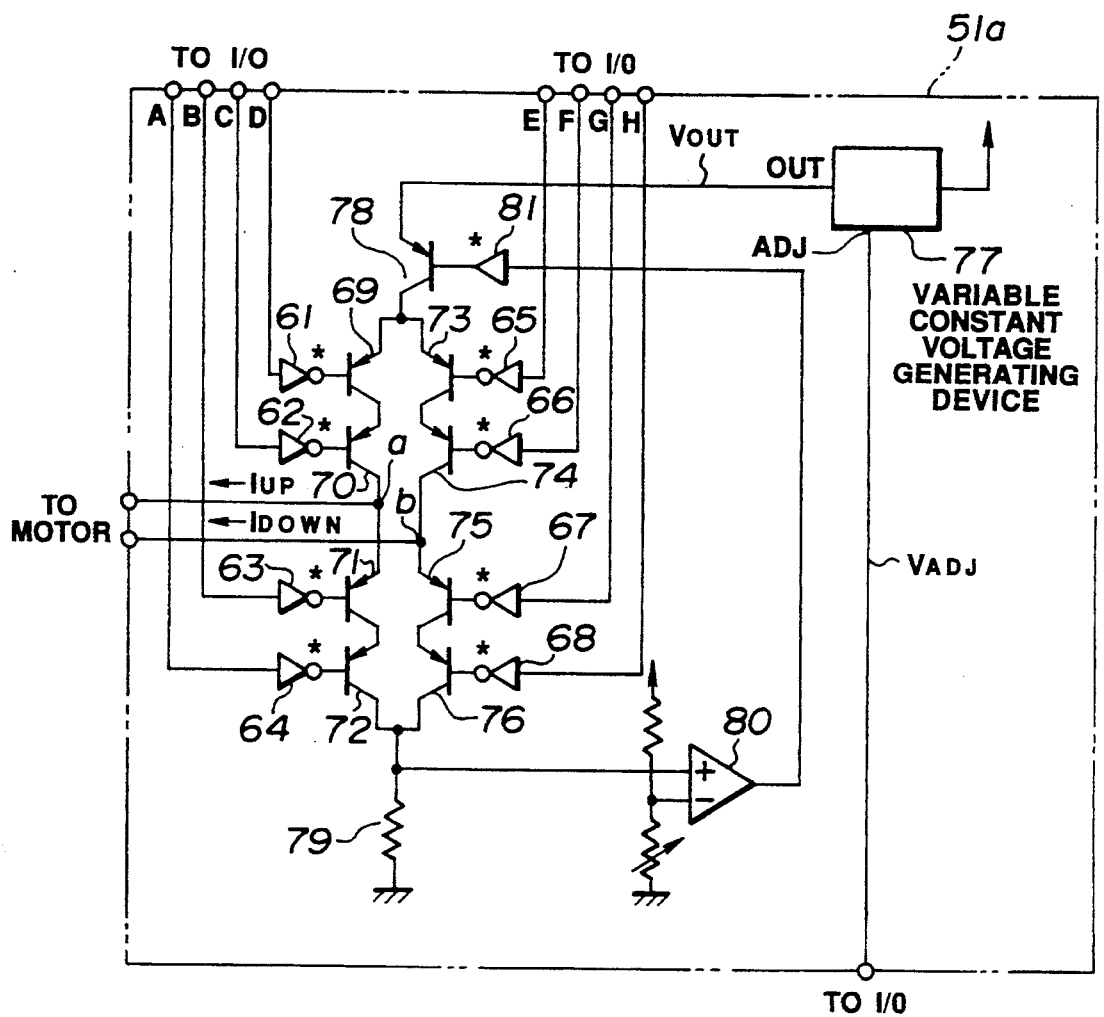
FIG. 16 is a circuit diagram showing the formation of a motor driving circuit relating to the fourth embodiment.

FIG. 16 is a circuit diagram showing the formation of a motor driving circuit according to the fourth embodiment.

The fourth embodiment is different from the third embodiment in only the formation of the motor driving circuit, which shall be explained below, but is the same as the third embodiment in the other formations and operations and shall bear the same reference numerals and shall not be explained here.

As shown in FIG. 16, the motor driving circuit 51a of the fourth embodiment is of the formation of the motor driving circuit 51 (see FIG. 13) of the third embodiment except for the constant speed controlling circuit 84 and initial switching circuit 75. Furthermore, a table shown in Table 1, is memorized in advance by such memorizing means as, for example, the ROM 55 and an analog voltage D/A-converted through the I/O 52 in response to this table is input into the ADJ terminal of the variable constant voltage generating device 77. The other formations are the same as in the third embodiment.

TABLE 1

| Bending angle | Motor rotating position | Number of revolutions of motor per bending angle of 10° | Voltage |
|---|---|---|---|
| 0° | 0 | — | 0 V |
| UP 10° | 0.10 | 0.10 | 1.10 V |
| UP 20° | 0.21 | 0.11 | 1.11 V |
| : | : | : | : |
| : | : | : | : |
| UP 200° | 2.72 | 0.18 | 1.18 V |

The motor rotating position represents a numerical value corresponding to the potentiometer 58 and the number of revolutions of the motor per bending angle of 10° represents a variation in the amount of the motor rotating position until a bending angle of 10° in the next step.

In the thus formed fourth embodiment, as the bending angle is detected by the potentiometer 58 and the voltage responding to the table shown in Table 1 is fed as V ADJ by the CPU 54, when the bending angle is small, the motor 22 will rotate slowly but, when the bending angle is large, it will rotate quickly. Therefore, the actual bending speed of the bendable part will be fixed.

For brevity, only the operation in the up direction has been explained but the same operation will be made by using the same table also in the down direction and right and left direction.

The other operations and effects are the same as in the third embodiment.

FIGS. 17 and 18 relate to the fifth embodiment of the present invention. FIG. 17 is a formation diagram showing bending pieces of a bendable part. FIG. 18 is a block diagram showing the formation of bending angle detection.

In the fifth embodiment, a bending angle detecting circuit 105 shown in FIG. 18 is provided in place of the rotation angle detecting circuit in the first embodiment shown in FIG. 1 or the second embodiment shown in FIG. 7. With regard to the same formation and operation as those in the first embodiment or second embodiment, drawings and explanation are omitted and only different points will be explained below.

FIG. 17 shows a plurality of joint pieces which are provided in the bendable part 8 and rotatably combined with each other. A plurality of wires (not illustrated) are inserted into the joint pieces 100 . . . , 101 shown in FIG. 17. Each wire is fixed to a joint piece 101 in the tip part side. The joint piece 101 is fixed within the tip part 9. The wire is pulled, so that the plurality of joint pieces rotate. Then, the bendable part 8 is bent.

The joint pieces 100 . . . , 101 are rotatably connected with each other by rotation axes (not illustrated). A potentiometer 102 is provided in each rotation axis. As shown in FIG. 18, a voltage of +E is applied to the end of the potentiometer 102 and a voltage of −E is applied to the other end of the potentiometer. An intermediate terminal of the potentiometer is connected to an adding circuit 104 through an A/D converter 103. The output of the adding circuit 104 is fed to the bending angle detecting circuit 105.

The aforesaid potentiometer 102 rotates in agreement with each angle of $\theta_0$, $\theta_1$, $\theta_2$, and $\theta_3$, among the joint pieces 100 . . . , 101. The sum of the aforesaid angles $\theta_0$, $\theta_1$, $\theta_2$, and $\theta_3$, is a bending angle $\theta$ of the bendable part 8. When the angle $\theta$ is equal to 0° (the bendable part 8 is straight), the voltage supplied from the intermediate terminals of the potentiometer 102 is zero. When the bendable part 8 is bent upward to provide a maximum bending angle, a voltage of +E is output. When the bendable part 8 is bent downward to provide a maximum bending angle, a voltage of −E volt is output. The aforesaid output voltage of the aforesaid intermediate terminal is converted into digital signals (data) by the A/D converter 103 and supplied to the adding circuit 104. The adding circuit 104 adds the data of the A/D converter 103 and supplies the data to the bending angle detecting circuit 105. The bending angle detecting circuit 105 detects the bending angle using the output of the adding circuit 104.

Here, as shown in FIG. 17, the bending angle $\theta$ of the bendable part 8 is equal to ($\theta_0"\theta_1+\theta_2+\theta_3$). Therefore, the bending angle $\theta$ can be obtained as in the aforesaid formation by adding the bending angles among the respective bending pieces. Although the angles are indicated as $\theta_0$ to $\theta_3$ in the example in the drawing, a greater number of angles may be used.

In this formation, when the bendable part 8 is straight, each intermediate terminal of each potentiometer 102 has a potential of zero volts and, therefore, the output of the adding circuit 104 becomes zero.

When the bendable part 8 bends upward such as to maximize the banding angle, the potentiometer 102 outputs +E volts and the adding circuit 104 outputs a voltage data "+4E". On the other hand, when the bendable part 8 bends downward to make the bending angle the maximum, the potentiometer 102 outputs −E volts and the adding circuit 104 outputs a voltage data "−4E".

The bending angle detecting circuit 105 converts the voltage data of the adding circuit 104 into a bending angle data. For example, if the maximum upward bending angle is equal to 180° and the maximum downward upward bending angle is equal to 180°, a bending angle can be converted using a relational expression (180×(E0+E1+E2+E3))/4E. Accordingly, in the case where (E0+E1+E2+E3) is equal to +E3, the bending angle is +135°.

In this embodiment, the motor 22 is driven in the aforesaid control circuit 30 or 30a so as to ensure a constant bending angle speed based on the bending angle detected by the bending angle detecting circuit 105, even when the bendable part is nearly straight.

A bending wire is slightly slack when the bendable part is straight because tension is not applied to the wire. Therefore, even in the case in which the bendable part is straight as well as the case in which the part is slightly bent to provide some bending angle, the fat that the wire is similarly pulled in both cases makes the determination of a nearly straight bendable part difficult because of the slack of the wire.

Therefore, in the endoscope of this embodiment, in order to keep the bending responsibility constant at angles in the vicinity of the straight bendable part, the rotation of the motor 22 is driven to speed up the bending speed at angles in the vicinity of the straight bendable part more than at other predetermined bending angles. In bending angle ranges other than in the vicinity of the straight bendable part, the rotation speed of the motor 22 is controlled to be slower than when in the vicinity of straight bendable part. In this embodiment, a bendable part can be bent at a constant bending angle speed in the bendable range, including that of a nearly straight bendable part.

Since other formations and operational effects are identical to those in the first embodiments, explanation is omitted.

If the rotation speed of a motor is set to be speeded up only in the vicinity of straight bendable part, the apparatus of the first and second embodiments can obtain similar effect to the fifth embodiment.

In this invention, it is clear that working modes different in a wide range can be formed on the basis of the spirit of the invention. This invention is not restricted by its specific working modes except by the appended claims.

What is claimed is:

1. An electrically bendable endoscope apparatus including an endoscope having an insertable portion comprising:

a bending mechanism for bending a bendable part of said insertable portion of said endoscope;

driving means for driving said bending mechanism, said driving means including a variable voltage power source for producing an output voltage value for driving said bending mechanism;

operating means for providing an instruction for bendably operating said bendable part;

bending angle detecting means for detecting the bending angle of said bendable part;

memorizing means for memorizing the relation between the output voltage value of said variable voltage power source and the bending angle detected by said bending angle detecting means; and controlling means for controlling said driving means to drive said bending mechanism so as to maintain a fixed predetermined speed, said controlling means selecting the output voltage value of said variable voltage power source stored in said memorizing means corresponding to the bending angle detected by said bending angle detecting means.

* * * * *